US010314568B2

(12) United States Patent
Vogtherr

(10) Patent No.: US 10,314,568 B2
(45) Date of Patent: Jun. 11, 2019

(54) SURGICAL RETRACTOR WITH REMOVABLE ACTUATING ELEMENT

(71) Applicant: Aesculap AG, Tuttlingen (DE)

(72) Inventor: Robert Vogtherr, Tuttlingen (DE)

(73) Assignee: Aesculap AG (DE)

( * ) Notice: Subject to any disclaimer, the term of this patent is extended or adjusted under 35 U.S.C. 154(b) by 0 days.

(21) Appl. No.: 15/024,235

(22) PCT Filed: Sep. 18, 2014

(86) PCT No.: PCT/EP2014/069905
§ 371 (c)(1),
(2) Date: Mar. 23, 2016

(87) PCT Pub. No.: WO2015/044026
PCT Pub. Date: Apr. 2, 2015

(65) Prior Publication Data
US 2016/0213365 A1 Jul. 28, 2016

(30) Foreign Application Priority Data
Sep. 27, 2013 (DE) .......................... 10 2013 110 717

(51) Int. Cl.
*A61B 17/02* (2006.01)
*A61B 17/00* (2006.01)

(52) U.S. Cl.
CPC ...... *A61B 17/0206* (2013.01); *A61B 2017/00407* (2013.01); *A61B 2017/00477* (2013.01)

(58) Field of Classification Search
CPC ....................................... A61B 17/02–17/0293
(Continued)

(56) References Cited

U.S. PATENT DOCUMENTS

| 4,747,394 A | 5/1988 | Watanabe |
| 5,052,373 A | 10/1991 | Michelson |

(Continued)

FOREIGN PATENT DOCUMENTS

| CA | 2583285 A1 | 4/2006 |
| CN | 1615802 A | 5/2005 |

(Continued)

OTHER PUBLICATIONS

German Search Report dated Mar. 28, 2014 for German Application No. 10 2013 110 717.6 with translation.
(Continued)

*Primary Examiner* — Nicholas J Plionis
(74) *Attorney, Agent, or Firm* — RatnerPrestia

(57) ABSTRACT

A retractor features at least two retractor arms whose proximal end portions are fixed or integrally formed on opposite ends of a crossbar for adjusting the distance between the retractor arms, and a drive unit whose case is mounted on the crossbar and whose gearing is in operative connection with a length adjustment mechanism to be operated by a separate actuation element which can be brought into engagement with a gearing input element movably inserted in the case. The gearing input element is accessible on at least one outer side of the casing. The gearing input element is designed such that it is substantially flush with the case's outer side or is recessed into the case interior. It has its exposed side provided with recesses, at least one of which has an undercut which enters a manually detachable latching engagement with a force transmission protrusion of the actuation element.

16 Claims, 4 Drawing Sheets

Figure 1:
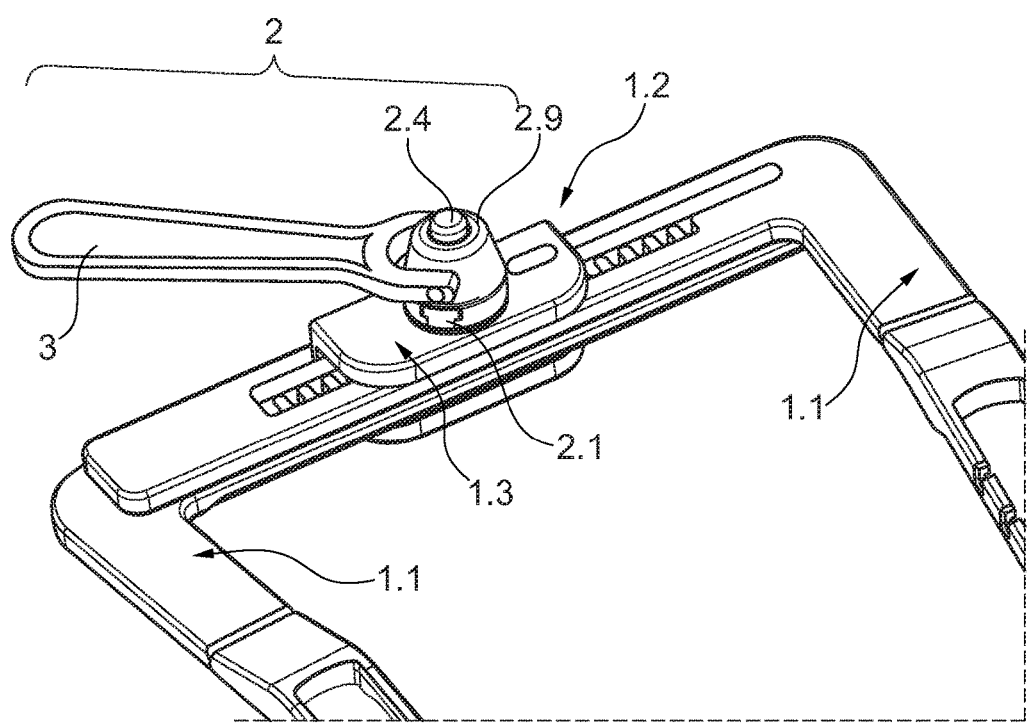

(58) Field of Classification Search
USPC .................................................. 600/201–246
See application file for complete search history.

(56) References Cited

U.S. PATENT DOCUMENTS

| | | | |
|---|---|---|---|
| 7,575,546 B2 | 8/2009 | Schoellhorn | |
| 7,922,658 B2 | 4/2011 | Cohen et al. | |
| 2009/0203969 A1 | 8/2009 | Cohen | |
| 2010/0030184 A1* | 2/2010 | Boulis ................ | A61B 17/0206 604/500 |
| 2010/0185060 A1* | 7/2010 | Farley ................ | A61B 17/0206 600/228 |
| 2010/0204548 A1* | 8/2010 | Bonadio ............ | A61B 17/3423 600/201 |
| 2010/0268241 A1* | 10/2010 | Flom .................. | A61B 17/3421 606/104 |
| 2013/0046147 A1* | 2/2013 | Nichter ............... | A61B 1/32 600/228 |

FOREIGN PATENT DOCUMENTS

| | | |
|---|---|---|
| CN | 201157372 | 12/2008 |
| EP | 1471831 | 11/2004 |
| JP | H04500014 A | 1/1992 |
| JP | H09299373 A | 11/1997 |
| JP | 3077381 B2 | 8/2000 |
| JP | 2004255173 A | 9/2004 |
| WO | 9001298 A1 | 2/1990 |
| WO | 2009124244 | 10/2009 |
| WO | 2014146824 | 9/2014 |

OTHER PUBLICATIONS

International Search Report issued in related International Application No. PCT/EP2014/069905, dated Dec. 5, 2014.
Chinese Office Action for Chinese Application No. 201480058931.5, dated Nov. 30, 2017 with translation, 18 pages.
Notification of Reasons for Rejection for Japanese Application No. 2016-517514, dated Jun. 12, 2018, with English translation, 6 pages.

* cited by examiner

SURGICAL RETRACTOR WITH REMOVABLE ACTUATING ELEMENT

RELATED APPLICATIONS

This application is the U.S. National Phase entry of International Application No. PCT/EP2014/069905, filed Sep. 18, 2014, which is related to and claims the benefit of priority of German Application No. 10 2013 110 717.6, filed Sep. 27, 2013. The contents of International Application No. PCT/EP2014/069905 and German Application No. 10 2013 110 717.6 are incorporated by reference herein for all purposes.

FIELD

The present invention relates generally to a retractor, and more specifically to a surgical retractor having at least two retractor arms.

BACKGROUND

In many heart surgery procedures, the sternum of the patient has to be severed in the longitudinal direction and then the halves of the sternum including the ribs extending therefrom have to be spread apart in order to allow the operating surgeon to work on the heart. For the purpose of spreading said operation opening, retractors (also referred to as blockers or spreaders) are used.

It may happen that the operating surgeon works for several hours in said operation area which is kept open by a retractor. In order to avoid the retractor itself being interfering or obstructive, it should lie on the patient as flat as possible. As experience teaches, the operating surgeon frequently puts down his heels of hand on the retractor frame for protecting the wrists. Especially any small angular contours or any shapes protruding in uncomfortable manner bar the way to do so.

Moreover, the retractor must not have any contours which would cause surgical threads and suture material being caught or hooked in. This is why all geometries should be designed so as to be smooth and planar.

The frame of the retractor, usually consisting of one or more racks which form a longitudinally adjustable crossbar, two valve arms which are formed on the longitudinal ends of the crossbar or fixed thereon, and a drive box which is mounted on the crossbar, do not present a noteworthy dimensioning problem. Such a retractor is relatively flat with all known embodiments.

The only component which is always considered annoying by all operating surgeons with all the retractors being available on the market, is the drive crank by means of which the longitudinal displacement of the crossbar for spreading the sternum is manually performed. It has to be large enough so that it can be grasped well and fits ergonomically in the hand to some extent. With this, it projects some centimeters beyond the flat drive box and is the only component which protrudes from the flat silhouette of the retractor.

As a very small, space-saving crank indeed would be less interfering, but is not practicable for handling, a detachable crank is the best technical solution so far. EP 1 471 831 B1 discloses a drive of a blocker of the present type, in which the crank can be taken off from the drive associated to the retractor. This is a drive in which a square shaft projects from a drive box which is mounted on the retractor. A crank comprising a correspondingly mating female square is fitted in form-locking fashion on said square shaft. As the case may be, the two elements also comprise a latching element, e.g. a ball pressure piece and a mating feature as latching position for securing the assembled state.

However, the detachable crank according to EP1 471 831 B1 has the disadvantage that it indeed reduces the interfering contour of the drive when removed, but does not completely eliminate it. A square shaft or a bolt of any other shape will always exist and may be perceived by the operating surgeon as inexpedient. In particular, the crank in the assembled state is usually not reliably adapted on the square shaft of such a drive. The form-locking plug connection is only effected in one plane. Removing the crank from the drive (from the square shaft), i.e. the inversion of the plug-in process, is not counteracted at all or only to a very low degree possibly by means of a ball pressure piece or similar latching element, in this case in force-locking manner. In any case, said latching element does not have an autonomous actuation means, i.e. it is automatically operated upon pulling off the crank from the crank stud and hence represents only a weak resistance. This is why the crank, determined by the system, can be pulled off just as easy as it is attached. In use, however, the operating surgeon will exert onto the crank not only radial forces, but also unintentional compressive and tensional forces in the longitudinal direction of the square shaft axis. This is why the crank may come loose from the assembled state in case of an insufficient securing and impede the work with the retractor.

Basically, there is the possibility to secure the crank on the square shaft by means of a shaft nut, for instance. It would also be possible to provide splints or similar securing elements preventing any unintentional removal of the crank from the square shaft (crank stud). This form of axial securing, however, always requires a second hand and/or a second assembly/disassembly step, reducing the functionality of the retractor.

SUMMARY

It is therefore the object of the present invention to provide a retractor which has a higher functionality vis-à-vis the previously mentioned prior art.

One aim of the invention is to improve the manageability of the retractor in use.

A further aim of the invention is to enhance the operational safety of the retractor. In particular, the invention is aimed at providing a crank which includes an actuation element and is able to be taken off from a retractor drive, which cannot come loose in unwanted or unintentional manner from the drive and which when taken off generates a really flat drive box/drive case without any jutting contours.

As a result, the retractor according to the invention is supposed to not present any hindrances to the operating surgeon, so that the event of surgical threads and suture material getting caught or hooked in the area of the drive can be excluded to the greatest possible extent.

The basic idea of the invention is to enhance the functionality of the retractor first in that the gearing input element (input disk) of the drive firmly mounted on the retractor is set back into the drive case in order to achieve a zero protrusion with respect to the case's outer side or only a negligible one. This will be achieved preferably in that the gearing input element formed and supported as a rotary component in accordance with prior art has its face exposed toward outside the gearing case realized or provided with at least one recess which is adapted for transmitting a torque from the actuation element, e.g. the crank/lever, on the gearing input component/element, whereas the detachable crank is formed or provided with at least one protrusion which can be inserted into the at least one recess in a torque-proof manner.

With this, the torque-proof connection between the crank and the gearing input element is translocated, so to speak, from the crank into the gearing input element and hence into the drive case. Stated in other words, the square shaft known in prior art or the torque transmission wheel/bolt formed in any other way is not arranged on the gearing input element and would remain there in interfering manner even after having detached the crank, but is now provided on the crank and thus taken off together with it.

In order to be able to transmit a sufficient torque, it is required to make the force application areas on the gearing input component (input disc) as large as possible, so that the surface pressure does not overstrain the employed material, or, as an alternative to this, to design the torque transmission means such that a large lever arm is produced on the gearing input element.

Therefore, it is preferred to provide a retractor comprising at least two retractor arms whose proximal end portions are fixed or integrally formed on the opposite ends of a longitudinally adjustable crossbar for adjusting of the transverse distance between the retractor arms, and a drive unit (transmission gear) whose case is mounted on the crossbar and whose gearing (toothed wheel gearing) is in operative connection with a length adjustment mechanism of the crossbar in order to be manually operated by means of a separate actuation element (crank) which can be brought into engagement with a gearing input element which is movably inserted in the case, preferably rotatably inserted therein, which gearing input element is accessible to this end from outside on at least one outer side of the casing. As already explained above, the gearing input element is designed such that it is substantially flush with the case's outer side (maybe with a negligible projection) or is even set back into the case interior with respect to said case's outer side. In this way, there are no edges or similar obstacles where OP material such as suture threads could get caught. The surface of the drive case is realized to be consistently level, so that the manipulation of the retractor can be improved as well.

According to an aspect of the invention possibly to be claimed independently, provision is made that the gearing input element is rotatably held in the gearing case and comprises at least one recess at its face exposed towards outside, said recess being adapted as a force/torque introduction member for the actuation element. This means that no part of the gearing input element projects from the case (not even temporarily). The recess may have a shape which differs from a circular shape as shown by example (e.g. a multi-edge profile or the like), in order to be received in a positive-locking fit with the actuation element (crank) in the rotational direction. In this case, the at least one recess is centrally arranged on the gearing input element with respect to the rotary movement. As an alternative or in addition, a number (plurality) of recesses is provided which are spaced in the circumferential and/or radial direction of the preferably circular gearing input element, said recesses being provided as force/torque introduction members for the actuation element and generating a kind of a lever arm due to their mutual distance. This allows to introduce higher torques into the gearing input element and/or to give the individual recesses smaller dimensions and a smaller depth of penetration in the gearing input element. This in turn allows to give the gearing input element a plate-shaped or disc-shaped design (flat with respect to its diameter) and hence realize the gearing case in a correspondingly slim design. This means a further improvement of the manageability of the retractor.

It is preferred that the actuation element is implemented as a sort of crank or ratchet whose one end portion is provided with a handle and whose other end is provided with an engagement head (crank head) comprising at least one, preferably two protrusions which can be simultaneously inserted into at least two of the recesses in order to transfer a torque to the gearing input element.

According to an aspect of the invention possibly to be claimed independently, provision is made that at least one recess on the side of the drive unit is formed with an axially acting undercut and at least one protrusion on the side of the actuation element is formed with an axially acting detent edge such the detent edge engages the undercut upon inserting the at least one protrusion into the at least one recess and in this way prevents/impedes the protrusion from being unintentionally pulled out of the recess.

Preferably, provision is made that the at least one protrusion comprising the detent edge can be moved in and contrary to the lock-in direction (radially with respect to the rotary movement of the gearing input element), in order to be able—irrespective of its movement regarding inserting/slipping off the protrusion in/from the recess—to be manually brought at least into one disengagement position with respect to the undercut. This means that an automatic actuation of the latching due to slipping off the actuation element from the gearing input element, as provided in prior art, is excluded according to the invention, as releasing the latching requires an independent, separate manual actuation. This prevents the actuation element from being unintentionally slipped off during use.

The invention will be explained in more detail below on the basis of a preferred exemplary embodiment with reference to the accompanying Figures, while also referring to alternative designs which are not illustrated figuratively.

BRIEF DESCRIPTION OF THE DRAWING FIGURES

Figure 2:
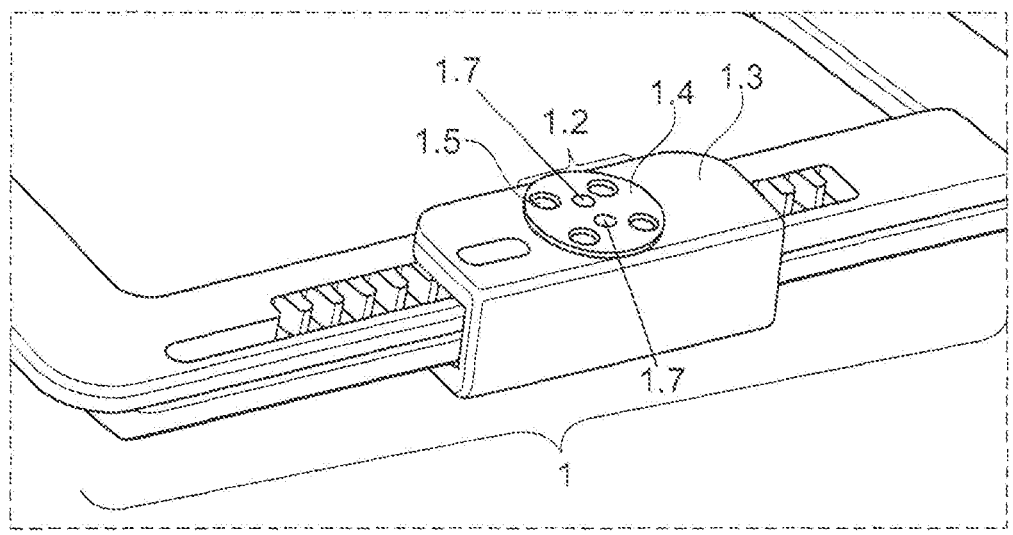
Figure 3:
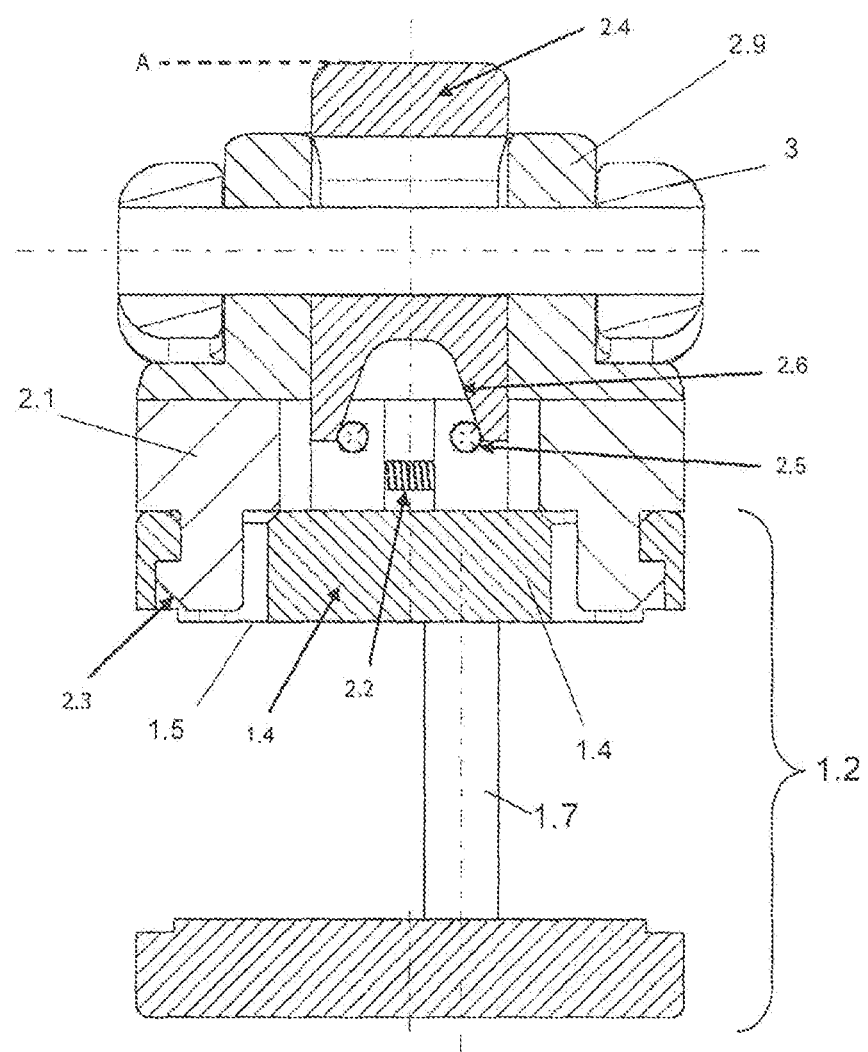
Figure 4:
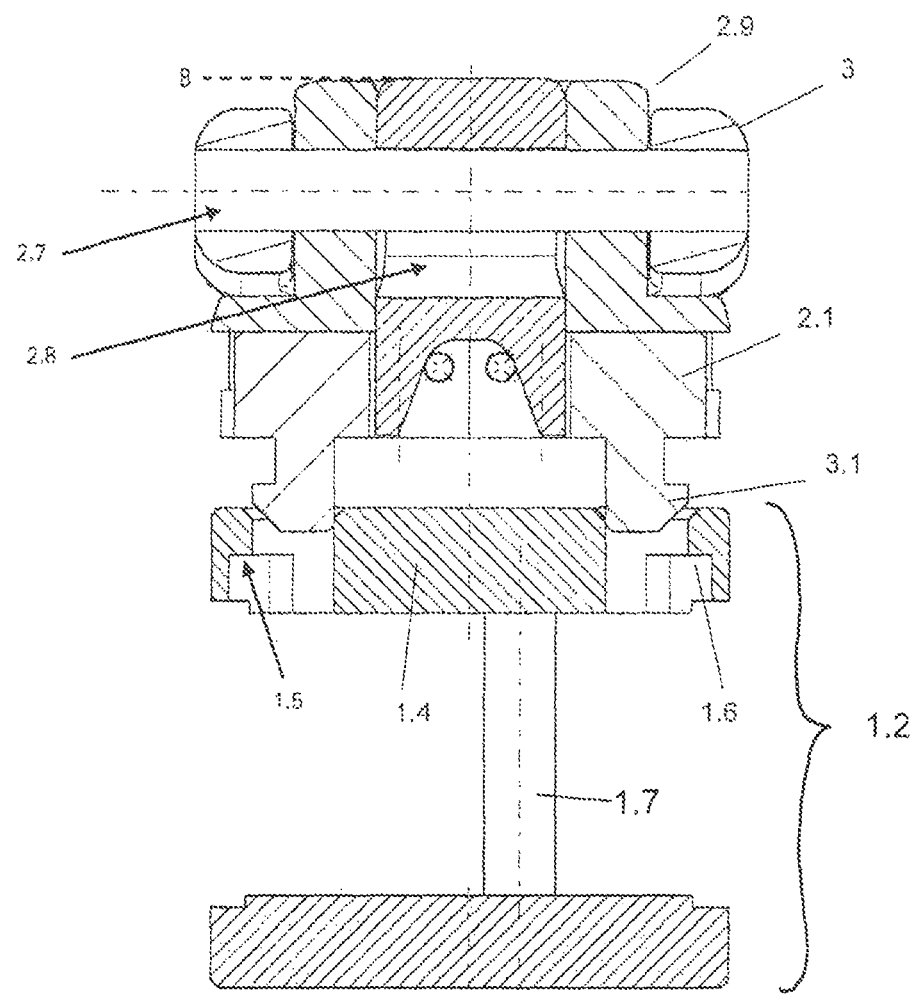

FIG. 1 shows a perspective view of a retractor according to a preferred exemplary embodiment of the present invention, FIG. 2 shows a drive unit of the retractor according to FIG. 1 in an enlarged view, FIG. 3 shows a cross-section of an actuation element, e.g. a crank, according to a preferred exemplary embodiment of the present invention in a locked or engaged position comprising the gearing input element of a retractor-side drive unit and FIG. 4 shows a cross-section of the actuation element of FIG. 2 in a separately and individually effected disengaged position together with the gearing input element.

DETAILED DESCRIPTION

According to FIG. 1, the retractor 1 according to the invention substantially consists of two retractor arms 1.1 which are provided or can be provided at their distal free ends with patient engagement means (not shown in further detail) and which have their proximal ends connected to a longitudinally adjustable crossbar or to a crossbar comprising a longitudinally adjustable mechanism; it is also possible that said proximal ends are formed to result in such a crossbar. Specifically, the two retractor arms 1.1 each define an angled element comprising a patient engagement leg representing the retractor arm and a crossbar leg extending at right angles thereto and representing a part of the crossbar. At least one of the crossbar legs is formed with a rack toothing (as length adjustment mechanism), with the two crossbar legs being held so as to be longitudinally shiftable relative to each other. Further, a central portion of the crossbar constituted by the two crossbar legs has a drive unit 1.2 mounted thereon which comprises a gearing (not shown in further detail) acting on the at least one rack toothing and hence shifting the one crossbar leg with respect to the other crossbar leg in the longitudinal direction. The gearing (not illustrated) is accommodated in a drive box or case 1.3 which is fixed to the crossbar leg that is realized without a toothing.

According to. 2, the drive unit 1.2 of the retractor 1 comprises a gearing input element, in the present case in the form of an upper/frontal disc 1.4 which is held in the drive box/drive case 1.3 so as to be rotatable around its center axis and comprises a (flat) face which is exposed to/freely accessible from the outer side of the drive box 1.3; said flat face is essentially flush with the drive box 1.3 at least on said outer side and does not protrude from it or only to a negligible extent. In the present case, the exposed (circular) outer side of the gearing input element 1.4 is provided with a number of (four) recesses 1.5 which are preferably spaced at equal angular distances and are realized in the form of holes which are aligned to be perpendicular to the flat face and in the present case represent the corner points of a square on the circular upper side of the gearing input element 1.4. The recesses 1.5 constitute a torque input means for transferring a torque from an actuation element 2, i.e. a crank or ratchet, to the gearing input element 1.4. To this end, the recesses 1.5 generate a sort of imaginary lever arm whose length is equal to the distance of each two diametrically opposite recesses 1.4.

According to FIG. 1, the actuation element 2 formed to be separate from the drive unit 1.2 in turn comprises a handle lever 3 which has its one end provided with an element head (in the following referred to as crank head) 2.9 which in the present case according to FIGS. 3 and 4 comprises two engaging protrusions or pins (engaging elements) 2.1 which are formed thereon perpendicularly to the handle lever 3 and can be selectively inserted in two diametrically opposite recesses 1.5, as will be explained in more detail below. In this way, the crank 2 can be put on the drive unit 1.2/the gearing input element 1.4 in different angular positions depending on the number of the recesses 1.5.

In FIG. 1, the retractor 1 according to the invention is illustrated with the actuation element/crank 2 being seated/attached and in this case the protrusions/pins/studs etc. 2.1 of the crank 2 being inserted in the recesses 1.5 (not visible in FIG. 1) on the side of the gearing input element 1.4 to transfer a torque to the gearing input element 1.4. This inserted state is shown in FIGS. 3 and 4 in cross-section and will be explained in more detail below.

According to FIG. 3, 4, each of the recesses 1.5 (with a minimum number of one recess) comprises an undercut 1.6 which acts in the axial direction of the recess 1.5, whereas the protrusions or pins 2.1 of the actuation element (crank/ratchet) 2 which are to be inserted into the recesses 1.5 are realized with corresponding detent edges (hook-shaped detent lugs) 3.1 which can be brought into an axially acting locking engagement with the undercuts 1.6 upon inserting the protrusions 2.1 into the recesses 1.5 in order to prevent the protrusions 2.1 from being pulled out of the recesses 1.5.

Each detent edge/detent lug 3.1 or each protrusion 2.1 comprising a detent edge 3.1 can be moved from a locked position (in which an engagement with the corresponding undercut 1.6 is made or can be made, see FIG. 3) manually and separately, i.e. irrespective of the position where the protrusions 2.1 are inserted in the recess 1.5, to a disengaged position (see FIG. 4). To this end, the protrusions 2.1 of the crank 2 according to the present exemplary embodiment are guided in the crank head 2.9 in form-locking manner so as to be movable to and away from the associated undercut 1.6 (in the radial direction of the gearing input element 1.4), for instance in a dovetail guide (see FIG. 1). In this respect, it is to be noted that the undercuts 1.6 of each two diametrically opposed recesses 1.5 are positioned so as to face each other, i.e. the detent edges 3.1 of the crank-side protrusions 2.1 face away from each other in radial direction and hence are oriented toward the respective undercuts 1.6, so that the protrusions 2.1 have to move toward each other in the event of a (radial) disengagement movement thereof.

Consequently, a spring element 2.2 is arranged on the crank head 2.9 and inserted between two diametrically arranged protrusions 2.1 and pushes away said two protrusions 2.1 from each other in radially outward direction (into the latching position). The protrusions 2.1 comprise bevels or chamfers 2.3 in the area of their detent edges 3.1 at their lower sides facing the respective undercuts 1.6, so that they are automatically shifted/moved radially inwards contrary to the spring force upon inserting them into the recesses 1.5 of the disc-shaped gearing input element 1.4 during the axial sliding movement on the undercuts 1.6 and, after having put the crank 2 on the disc-shaped gearing input element 1.4, can latch in place in the undercuts 1.6 of the recesses 1.5 in spring-biased manner.

This form-locking latching scheme prevents any unwanted or unintentional release of the crank 2 and cannot be reversed by a mere pull-out process.

For detaching or releasing the crank 2 from the drive unit 1.2, the operating surgeon has to actuate an actuation element 2.4 on the crank 2. In the present exemplary embodiment, said actuation element 2.4 is designed as a push button or key and converts the direction of movement of the protrusions (engaging elements) 2.1 which lies in the plane of the handle lever 3 or crank head 2.9 into a movement of the push button 2.4 which is perpendicular thereto. Stated in other words, the push button 2.4 is supported to be axially shiftable substantially centrically in the crank head 2.9 between the two protrusions 2.1 and on the ball head side facing away from the protrusions 2.1 and hence can be moved in the longitudinal direction of the protrusions 2.1. Further, the push button 2.4 is in operative connection with both protrusions 2.1 by means of a force transmission system, whereby the axial movement of the push button 2.4 is transformed into a movement of the two protrusions 2.1 which is perpendicular thereto (i.e. in the radial direction).

If said push button 2.4 is pressed, both protrusions 2.1 (engaging elements) will be moved against the spring force simultaneously and symmetrically with respect to the disc-shaped gearing input element 1.4 radially inward to the disengagement position. In this actuation position, they do not have any contact to the undercuts 1.6 and can be guided through or pulled out of the recesses 1.5 by lifting the crank 2.

To this end, the force/movement transmission system is designed as follows:

The push button 2.4 comprises two sliding edges or surfaces 2.6 which extend in its longitudinal direction or direction of actuation and diverge at an acute angle in the direction of actuation and represent a sort of guiding piece. Furthermore, each protrusion 2.1 comprises a dog or transverse pin 2.5 which rests against the respectively facing sliding edge 2.6 of the actuator button 2.4. If the actuator button 2.4 is pressed, the sliding edges 2.6 slide on the respectively abutting transverse pins 2.5. However, as the sliding edges 2.6 do not extend in perfect parallelism to the direction of actuation of the button 2.4, but at an acute angle thereto, the longitudinal movement of the sliding edges 2.6 results in a superimposing transverse movement of the protrusions 2.1 due to the sliding contact of the transverse pins 2.5 on the sliding edges 2.6, i.e. the sliding edges 2.6 have the function of wedges exerting a tensile or compressive force on the protrusions 2.1 against the spring 2.2.

By means of the spring(s) 2.2 between the protrusions (engaging elements) 2.1, the transverse pins 2.5 in the protrusions (engaging elements) 2.1 and the oblique sliding faces 2.6 in the lower area of the push button 2.4, against which the transverse pins 2.5 rest, the push button 2.4 itself is also resiliently supported and returns to its initial position A according to FIG. 3 after actuation. The actuation position B according to FIG. 4 can be defined when the two protrusions (engaging elements) 2.1 come to stop centrally, representing the point up to which the push button 2.4 can be pressed or vertically moved.

The initial position A which exists due to the spring 2.2 if the push button 2.4 is not manually operated, has to be defined by an upwardly acting stop on the push button 2.4 or an externally acting stop on the protrusions (engaging elements) 2.1.

A space-saving and cost-effective possibility is to insert a pin 2.7 transverse to the actuator button 2.4 into the crank head 2.9, which penetrates an elongated hole 2.8 of the push button 2.4, with the respective ends of the elongated hole defining the maximum actuation position and non-actuation position of the push button 2.4. Consequently, the push button 2.4 when actuated moves in spring-assisted manner out of the crank head (according to FIG. 3 vertically upward) until the end of the elongated hole 2.8 reaches the pin 2.7. This is the moment at which the initial position is established. Said pin 2.7 also serves for mounting the handle lever 3 on the crank head 2.9.

At this point, some modifications shall be mentioned which are conceivable alternatively or in addition to the previously described features.

The illustrated exemplary embodiment comprises two crank-side protrusions which each are provided with a detent edge and hence has to be movably guided on the crank head. Basically, it is also sufficient if only one of the protrusions has a detent edge. In this case, said one protrusion could be arranged preferably centrally between two further protrusions and only fulfil the function of preventing a slipping off (no transmission of torque).

It is also conceivable that the protrusions are not supported in movable fashion, but only the detent edge is movably supported on the protrusion concerned, whereas the protrusions themselves are fixedly held/formed on the crank head. Finally, a pivoting movement of the protrusions may also be provided instead of a shifting movement of the protrusions.

As already stated at the outset, the formation of several spaced recesses (engagement points for the crank) provide for a large effective lever arm on the gearing input element, so that the recesses can be formed to be small and have a low depth and still are able to transmit high torques. This allows to give the gearing input element a flat, disc-shaped design. In the case of only one central recess, however, it is conceivable to realize it in an out-of-round shape and in this way bring about a torque-proof form-fit with the inserted protrusion of the crank.

In summary, the disclosure relates to a retractor comprising at least two retractor arms whose proximal end portions are fixed or integrally formed on the opposite ends of a longitudinally adjustable crossbar for adjusting the transverse distance between the retractor arms, and a drive unit whose case is mounted on the crossbar and whose gearing is in operative connection with a length adjustment mechanism of the crossbar in order to be manually operated by means of a separate actuation element which can be brought into engagement with a gearing input element which is movably inserted in the case, preferably rotatably inserted therein, which gearing input element is accessible to this end from outside on at least one outer side of the casing. According to the invention, the gearing input element is designed (in disc shape) such that it is substantially flush with the case's outer side or is recessed into the case interior with respect to said case's outer side. It has its exposed side provided with recesses, at least one of said recesses comprising an undercut which enters a manually detachable latching engagement with a force transmission protrusion of the actuation element comprising a detent edge during inserting it into the recess for preventing any unintentional extraction.

The invention claimed is:

1. A retractor crank assembly for longitudinally adjusting cross bar legs of a surgical retractor, the retractor crank assembly comprising:
   A. a drive unit for mounting on a pair of cross bar legs of a surgical retractor, the drive unit comprising:
      i. a drive case defining a flat top surface; and
      ii. a rotary component rotatably mounted in the drive case, the rotary component comprising a flat outer face that is flush with the top surface of the drive case and at least one recess exposed on the top surface; and
   B. a crank for detachable coupling to the rotary component in a releasable form-locking manner for transferring torque to the drive unit when manual force is applied to the crank, the crank comprising:
      i. a handle operable for imparting torque to the drive unit when the handle is coupled to the drive unit;
      ii. at least one protrusion for insertion into the at least one recess of the rotary component, the at least one protrusion movable between a locked position, in which the at least one protrusion is positioned to engage the recess and securely lock the crank to the drive unit, and an unlocked position, in which the at least one protrusion is positioned to disengage the recess and permit manual detachment of the crank from the drive unit; and
      iii. an actuation element in operable communication with the at least one protrusion,
   wherein, when the crank is detached from the drive unit, the flat top surface of the drive case and flat outer face of the rotary component are free of jutting contours, and
   wherein the actuation element comprises at least one sliding edge, and the at least one protrusion comprises a transverse pin that slidably engages the sliding edge, the at least one sliding edge configured to convert axial force applied to the actuation element into a transverse force against the transverse pin to displace the at least one protrusion between locked and unlocked positions.

2. The retractor crank assembly of claim 1, wherein the at least one protrusion comprises a first engagement surface and the at least one recess comprises a second engagement surface that engages the first engagement surface in a form-locking manner when the at least one protrusion is moved to the locked position.

3. The retractor crank assembly of claim 2, wherein the crank further comprises a biasing element exerting a biasing force that biases the at least one protrusion toward the locked position.

4. The retractor crank assembly of claim 3, wherein the at least one protrusion further comprises a beveled surface, the at least one protrusion being movable out of the locked position against the biasing force and toward the unlocked position in response to contact between the beveled surface and a wall of the at least one recess.

5. The retractor crank assembly of claim 4, wherein the first engagement surface comprises a detent edge, and the second engagement surface comprises an undercut defined in the at least one recess, the biasing element operable to move the detent edge to the locked position and into the undercut when the detent edge axially aligns with the undercut.

6. The retractor crank assembly of claim 5, wherein the actuation element is movable between a first position to displace the at least one protrusion against the biasing force and toward the unlocked position for manually detaching the crank from the rotary component, and a second position to permit the at least one protrusion to move toward the locked position in response to the biasing force for locking the crank to the rotary component.

7. The retractor crank assembly of claim 6, wherein the crank comprises a crank head, and the actuation element comprises a push button or key that is centrally located in and axially displaceable in the crank head.

8. The retractor crank assembly of claim 1, wherein the at least one protrusion comprises a first pin and a second pin, and the at least one recess comprises a first recess and a second recess, the first recess and the second recess being adapted to receive the first pin and the second pin, respectively.

9. A surgical retractor comprising:
A. at least two retractor arms comprising a first cross bar leg and a second cross bar leg, the first cross bar leg formed with a racked toothing;
B. a drive unit mounted on the first and second cross bar legs so as to connect the first and second cross bar legs in a longitudinally adjustable manner, the drive unit comprising:
 i. a drive case defining a flat top surface;
 ii. a rotary component rotatably mounted in the drive case, the rotary component comprising a flat outer face that is flush with the top surface of the drive case and at least one recess exposed on the top surface; and
 iii. a gearing extending from the rotary component and into the drive case, the gearing acting on the racked toothing of the first cross bar leg for shifting the first cross bar leg longitudinally relative to the second cross bar leg in response to torque applied to the drive unit; and
C. a crank for detachable coupling to the rotary component in a releasable form-locking manner for transferring torque to the drive unit when manual force is applied to the crank, the crank comprising:
 i. a handle operable for imparting torque to the drive unit when the handle is coupled to the drive unit; and
 ii. at least one protrusion for insertion into the at least one recess of the rotary component, the at least one protrusion movable between a locked position, in which the at least one protrusion is positioned to engage the recess and securely lock the crank to the drive unit, and an unlocked position, in which the at least one protrusion is positioned to disengage the recess and permit manual detachment of the crank from the drive unit; and
 iii. an actuation element in operable communication with the at least one protrusion,
wherein, when the crank is detached from the drive unit, the flat top surface of the drive case and flat outer face of the rotary component are free of jutting contours, and
wherein the actuation element comprises at least one sliding edge, and the at least one protrusion comprises a transverse pin that slidably engages the sliding edge, the at least one sliding edge configured to convert axial force applied to the actuation element into a transverse force against the transverse pin to displace the at least one protrusion between locked and unlocked positions.

10. The surgical retractor of claim 9, wherein the at least one protrusion comprises a first engagement surface and the at least one recess comprises a second engagement surface that engages the first engagement surface in a form-locking manner when the at least one protrusion is moved to the locked position.

11. The surgical retractor of claim 10, wherein the crank further comprises a biasing element exerting a biasing force that biases the at least one protrusion toward the locked position.

12. The surgical retractor of claim 11, wherein the at least one protrusion further comprises a beveled surface, the at least one protrusion being movable out of the locked position against the biasing force and toward the unlocked position in response to contact between the beveled surface and a wall of the at least one recess.

13. The surgical retractor of claim 12, wherein the first engagement surface comprises a detent edge, and the second engagement surface comprises an undercut defined in the at least one recess, the biasing element operable to move the detent edge to the locked position and into the undercut when the detent edge axially aligns with the undercut.

14. The surgical retractor of claim 13, wherein the actuation element is movable between a first position to displace the at least one protrusion against the biasing force and toward the unlocked position for detaching the crank from the rotary component, and a second position to permit the at least one protrusion to move toward the locked position in response to the biasing force for locking the crank to the rotary component.

15. The surgical retractor of claim 14, wherein the crank comprises a crank head, and the actuation element comprises a push button or key that is centrally located in and axially displaceable in the crank head.

16. The surgical retractor of claim 9, wherein the at least one protrusion comprises a first pin and a second pin, and the at least one recess comprises a first recess and a second recess, the first recess and the second recess being adapted to receive the first pin and the second pin, respectively.

* * * * *